United States Patent [19]

Samson

[11] Patent Number: 4,819,616

[45] Date of Patent: Apr. 11, 1989

[54] BABY CALMER

[76] Inventor: Ilan Samson, 13, Eton Avenue, London NW3, England

[21] Appl. No.: 65,029

[22] PCT Filed: Aug. 12, 1986

[86] PCT No.: PCT/EP86/00476

§ 371 Date: Apr. 13, 1987

§ 102(e) Date: Apr. 13, 1987

[87] PCT Pub. No.: WO87/01044

PCT Pub. Date: Feb. 26, 1987

[30] Foreign Application Priority Data

Aug. 13, 1985 [EP] European Pat. Off. ........ 85110161.8

[51] Int. Cl.⁴ ............................................. A61M 21/00
[52] U.S. Cl. ...................................................... 600/28
[58] Field of Search ............... 128/1 C, 419, 420, 421, 128/422

[56] References Cited

U.S. PATENT DOCUMENTS

| 3,213,851 | 10/1965 | Curren | 128/1 C |
|---|---|---|---|
| 3,576,185 | 4/1971 | Shurlz | 128/1 C |
| 3,718,132 | 2/1973 | Holt et al. | 128/1 C |
| 4,034,741 | 7/1977 | Adams et al. | 128/1 C |
| 4,066,072 | 1/1978 | Cummins | 128/1 C |
| 4,124,022 | 11/1978 | Gross | 128/1 C |
| 4,141,344 | 2/1979 | Barbam | 128/1 C |
| 4,185,640 | 1/1980 | Kastrubin et al. | 128/1 C |
| 4,191,175 | 3/1980 | Nagle | 128/1 C |
| 4,289,121 | 9/1981 | Kupriyanovich | 128/1 C |
| 4,335,710 | 6/1982 | Williamson | 128/1 C |

OTHER PUBLICATIONS

International Search Report (2 pages) re PCT/EP 86/00476; this Search Report refers to U.S. Pat. Nos. 3,213,851 and 3,576,185, previously cited in the present case.

Primary Examiner—Edward M. Coven
Attorney, Agent, or Firm—Merchant, Gould, Smith, Edell, Welter & Schmidt

[57] ABSTRACT

A baby calmer comprises a source of sound adapted to calm a crying baby, with the sound taking the form of random noise or pseudo-random noise which extends over an audio frequency range preferably extending up to at least 10 kilohertz. The pseudo-random noise is generated for a short period at an initial level so that it is able to penetrate the baby's own crying and to attract its attention. The noise is subsequently switched to a lower level to lull the baby into sleep. After a few minutes the sound is switched off altogether.

14 Claims, 2 Drawing Sheets

BABY CALMER

FIELD OF THE INVENTION

The present invention relates to a baby calmer comprising a source of sound adapted to calm a crying baby.

BACKGROUND OF THE INVENTION

Research has been carried out into the use of recordings of, simulations of and synthesis of intra-uterine sounds for calming babies and has led to the marketing of cassettes containing such recorded sounds and of synthesizers for generating such sounds.

This form of sound has however generally only been found to be effective with babies of up to six weeks of age.

The existing intra-uterine sound methods using cassettes are cumbersome as they involve a cassette player, heavy usage of batteries, and are dangerous to run on mains close to the baby or obtrusive to the environment is located far away from the baby and set at an appropriate sound level. Furthermore, the cassettes are relatively expensive and the synthesizer even more so.

SUMMARY OF THE INVENTION

The object underlying the present invention is to produce a baby calmer which is at least as effective as and preferably more effective than the known intra-uterine sound devices, which can be used to calm babies which are substantially older than six weeks of age, which is easy to handle, which is unobtrusive, and which minimizes energy consumption so that it may readily be run on batteries.

In order to satisfy this object the present invention is characterised by a generator for generating random noise or pseudo-random noise over an audio frequency range extending up to at least several thousand hertz, preferably up to at least then thousand hertz; and by means for automatically reducing the level of said noise from an initial level to a lower level and subsequently to an imperceptible level, preferably zero.

The present invention is thus based on the concept that random noise or pseudo-random noise, typically referred to as white noise when extending over a wide range of frequencies or "pink noise" when extending over the range of audio-frequencies, has a calming effect on babies and young children. It has been noticed, for instance, that the most commonly pronounced sound used to calm or quiet people is "SHSHSH", an oral simulation of random noise. Moreover, it is believed that this is far superior to intra-uterine sound which contains the foetal heartbeat as a major component. This follows from oberservations that soft regular random sounds are more calming than regular beats, for example rain versus a dripping tap. Moreover, it is postulated that intra- uterine sound may in fact be far from ideal so far as its calming effect on a baby is concerned. It is postulated that a baby hears the intra-uterine sound for many months during the development of the foetus in the womb and is separated from the sound at the moment of birth. It is quite conceivable that this dramatic change would be disturbing to a baby (possibly similar to the disturbing adult experience of being present in an anechoic chamber) were he not "programmed" in some way to dissociate himself from this sound. Thus the unnatural recall of this sound experience might not be so welcome. This might also be the explanation for the observation that the calming effect of intra-uterine sound lasts for six weeks only.

However, the present invention does not rest with the recognition that white noise will exert a calming effect on a baby, instead it proposes the use of at least two different sound levels with the following aim. The initial higher sound level is intended to be a level comparable with that of a crying baby and sufficiently high that it is able to penetrate the babies own cry and, as it were, to attract the babies attention. Once this has been done, and observations have shown that a relatively short period of time is sufficient, normally a period of time in a range from 15 seconds to 45 seconds, it is proposed, in accordance with the invention, that the white noise generator be switched to a lower level which is sufficient to hold the babies attention and to lull it into sleep or at least a state of calmness. It is difficult to define the precise levels involved because the levels clearly depend on how close to the baby the device is positioned. Nevertheless, the initial level should be sufficient for the baby to hear it through its own crying and the lower level can be substantially lower, say approximately 20% of the initial level. Finally, the device should preferably switch off automatically which saves battery power and prevents residual low level random noise disturbing others.

It is believed that the baby calmer proposed herein is also sound from a psychological viewpoint. Babies cry because they want mothers attention; mothers want babies to stop crying; the mother has to come to the baby to switch the calmer on (the calmer would, for instance, normally be located in or adjacent the baby's cot) and this initial contact is good for both parties. The device does not come into the way of mother's attention and it does alleviate the one and common cause for the mother's antagonism, the excessive crying of the baby.

Observations have shown that when the baby has a specific cause for crying—such as hunger or pain, which needs more than passing attention, the effect of the white noise generator will not override the baby's crying "call".

Furthermore, it is believed that the harmlessness of low volume random noise is apparent, such random noise is, by definition, the most "unprogrammed" sound—it is that of a stream of water, wind through the trees, rain, etc.. The levels of random noise proposed herein are well within the safe and even pleasant limit.

Thus, it will be apparent from the foregoing, that the random noise which is to be used for the present invention preferably has the spectrum of white noise in a audio-frequency range (amplitude generally an exponentially decreasing function of wavelength) with no particular frequency predominating.

Preferably the means for reducing the level of noise from the initial level to the lower level is adapted to produce a step change in level. A timer circuit is conveniently provided for maintaining the initial level of noise at a substantially constant level for a short period of time, preferably in the range of 15 seconds to 1 minute and most preferably in the range from 30 seconds to 45 seconds. A second timer circuit, or the first timer circuit if suitably adapted, can be provided for maintaining the lower level of noise at a substantially constant level for a relatively longer period of time, preferably in the range from 2 to 7 minutes. As mentioned, the calmer is preferably switched on by a single switch and should switch off automatically at the end of the period of low level noise.

The time periods and modes of operation described above enable maximum effective calming while minimizing power consumption. This thus effectively extends the working life of the batteries.

In one specific form of the invention the noise generator is preferably packaged in a housing having the shape of a sea shell. This special shape of the housing is not only an attractive and compact design for placement into baby's cot it is also entirely consistent with the generation of white noise as can be recalled from the childhood experience of placing a sea shell to one's ear and listening to the "random noise" of the sea.

A specific form of the baby calmer is characterised in that the timer circuit comprises a first timer circuit that produces a first binary output having a high output for the duration of said initial noise level and a low output thereafter, a second timer circuit adapted to produce a second binary output having a high output for the duration of the initial noise level and for the duration of the low noise level, and a low output thereafter; voltage generating means coupled to said first and second binary outputs and adapted to generate a voltage output having a first level when both said binary outputs are high, a second lower level when only said second binary output is high, and a zero output when both binary outputs are low; a random noise source comprising a zener diode connected to said output voltage; amplifier means connected to said random noise source; cut-off filter means adapted to filter out frequency components above said audio frequency range and a converter for converting said amplified noise signal into audio noise. The heart of the baby calmer is thus a zener diode and the invention is based on the recognition that a zener diode is an excellent source of random noise, particularly if used without the normal bypass capacitor.

The voltage generating means preferably comprises an emitter follower in the form of a transistor having a base connected to said first and second binary outputs via respective coupling resistors, a collector connected to a source of power, preferably a battery, and an emitter coupled to said zener diode noise source.

The amplifier means expediently comprises first and second operational amplifiers connected in series with said cut-off filer disposed therebetween.

The converter for converting said amplified noise signal into audio noise may conveniently comprise a transformer which drives a speaker and which is driven in push-pull by two amplifiers. These two amplifiers together with the first and second operational amplifiers are usefully defined on a single chip, which is available at a relatively low cost.

Furthermore, each of said first and second timer circuits is conveniently formed by a respective pair of NOR-gates coupled together via a respective R.C. timing circuit, and these two pairs of NOR-gates are defined on a C-MOS chip.

DETAILED DESCRIPTION OF THE PREFERRED EMBODIMENT

Figure 1:
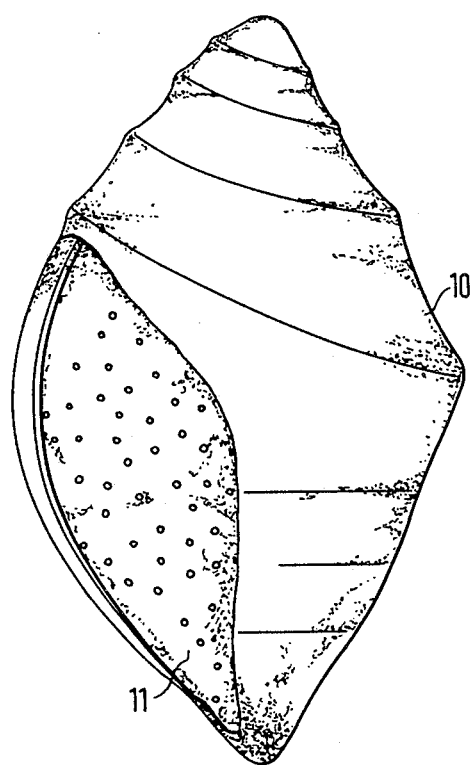
Figure 2:
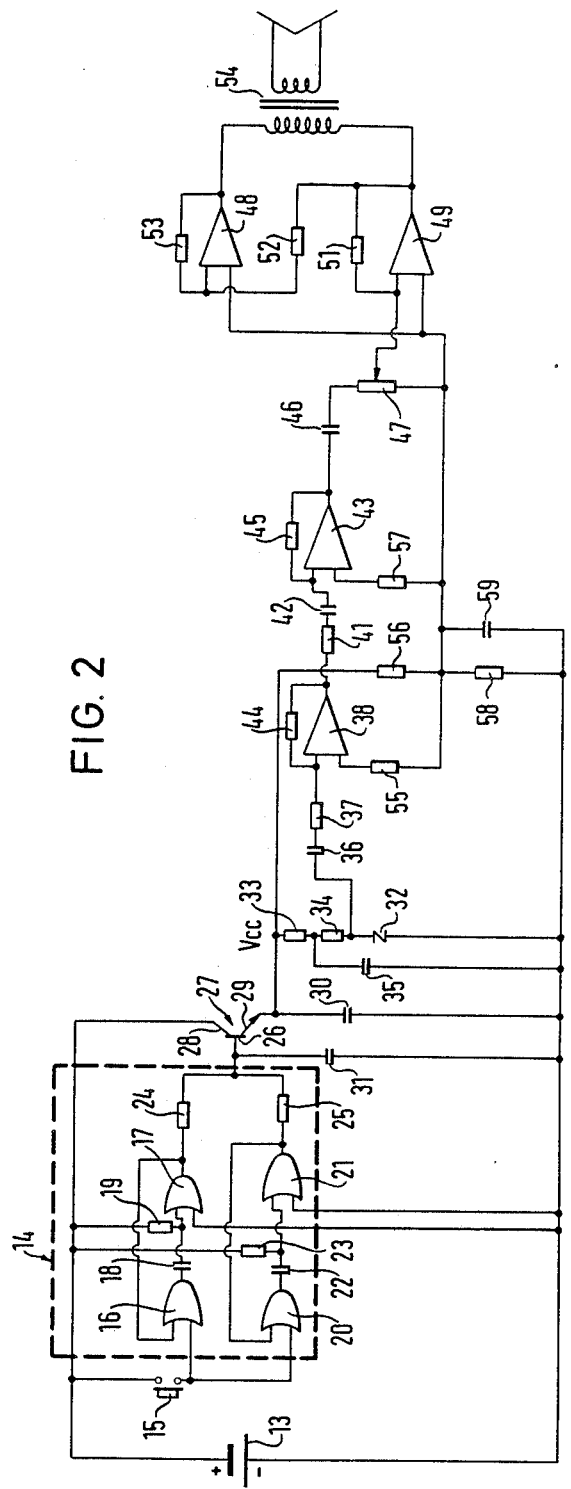

A specific embodiment of the invention will now be described in further detail by way of example only and with reference to the accompanying drawings which show:

FIG. 1 the preferred shape of a housing for the baby calmer,

FIG. 2 a circuit diagram of the internal components of a baby calmer.

As seen in FIG. 1 the baby calmer has the shape of a shell 10 with the speaker diaphragm (not shown) located behind a perforated cover 11 at the opening of the shell.

As seen in FIG. 2 the baby calmer is preferably powered by a battery 13 (although it could also be powered from a mains power supply (not shown)) and has a two stage timing circuit 14 which can be initiated by closing the push button switch 15. The first stage of the timing circuit is adapted to run for approximately 30 seconds and comprises two interconnected NOR-gates 16 and 17 which are connected together with a timing element comprising the resistor 19 and the capacitor 18 disposed therebetween. On pressing the button the output of the second flip-flop 17 goes high, the capacitor 18 is charged and holds the output high as the button is released. After a period of time determined by the R.C. circuit 18, 19 the capacitor 18 has discharged via the resistor 19 and the output of this timing stage is switched to a lower level (typically zero). The second timing stage comprises two further NOR-gates 20 and 21 with a second timing element comprising the capacitor 22 and the resistor 23 disposed therebetween.

The second stage of the timing circuit functions in the same way as the first stage and produces a time delay of 4 minutes. In other words, on depressing the button 15 the output of the NOR-gate 21 goes high and the capacitor 22 is charged. The output of the NOR-gate 21 remains high for 4 minutes due to the R.C. circuit 22, 23 until the capacitor 22 has discharged via the resistor 23 and the NOR-gate 21 passes into its low state. The outputs of the NOR-gates 17 and 21 (which are formed together with the NOR-gates 16 and 20 on a single C-MOS chip (type 4001)) are coupled via respective coupling resistors 24, 25 to the base 26 of an emitter follower in the form of a transistor 27. The collector 28 of the transistor 27 is connected to the battery potential and the emitter 29, which is connected to earth via a capacitor 30 so as to isolate any AC components delivers a voltage Vcc which can have three levels, namely a high level, an intermediate level and a zero level.

These three levels are determined by the current applied to the base of the transistor which is in turn determined by the three different possibilities for the states of the two outputs of the NOR-gates 17 and 21. These outputs can be either both high, or only one of them can be high and the other can be low, or both of them can be low. The base of the transistor is also connected to earth via a capacitor 31 to provide a leakage path for a.c. components. The voltage Vcc at the emitter is applied to a zener diode 32 via two resistors 33, 34 which are connected in series with the connection point between the two resistors being connected to earth via a capacitor 35. The function of this cpacitor/resistor arrangement is to prevent instability of the circuit. The zener diode is connected via a coupling capacitor 36 and a resistor 37 to one input of an operational amplifier 38. The output of the operational amplifier is connected via a filter formed by a resistor 41 and a capacitor 42 to the input of a second operational amplifier 43. The function of the filter is to cut off all frequencies above 10 kilohertz which helps save the battery power that is required. In the usual manner a small part of the output of the amplifier 38 is fed back to its input via a further resistor 44. Another resistor 45 is used in the same way with the second operational amplifier 43. The output of the second operational amplifier 43 is coupled via a capacitor 46 for D.C. isolation and a potentiometer 47 to a push pull driver circuit consisting of two further operational amplifiers 48 and 49 with the usual resistors 51, 52 and 53 which are connected to the primary winding of a transformer 54, the secondary winding of which is connected to a load speaker. The operational amplifiers 38, 43, 48 and 49 are also formed on a single chip (LM 432) and the arrangement of resistors 55, 56, 57, 58 and of the stabilizing capacitor 59 is provided to enable the chip to operate mid-rail as designed.

The above described circuit operates as follows:

On pressing the button switch 15 both timer stages are simultaneously started so that the outputs of the two NOR-gates 17 and 21 are both high. The output of the emitter follower stage is also high and thus the zener diode produces random noise which is amplified, filtered to cut out components above 10 kilohertz and amplified again before being supplied via the push-pull driver stage to the transformer which feeds the speaker for converting the electrical noise signal into an acoustic noise signal. After 30 seconds the output of the NOR-gate 17 goes low and the output level from the emitter follower is halved thus correspondingly reducing the level of noise generated by the speaker (the output of the emitter follower stage controls the gain of the amplifiers). After 4 minutes the output of the NOR-gate 21 also goes low, the output of the emitter follower is zero (the transistor is cut off) and noise generation ceases. I.e. the device has switched off automatically.

I claim:

1. A baby calmer device for producing when energized a single sequence of sound levels adapted to calm a crying baby, comprising generator means for generating noise over an audio frequency range extending up to at least two thousand hertz and reducing means connected to said generator means for automatically reducing the level of said noise by a single sequential step change from an initial sound level to a lower second sound level and subsequently by a single sequential step change to an imperceptible third sound level after which the device is automatically switched OFF.

2. A baby calmer device in accordance with claim 1 further including timer circuit means connected to said reducing means for maintaining said initial sound level of noise at a substantially constant level for a first period of time between 15 seconds and 1 minute.

3. A baby calmer device in accordance with claim 2, wherein said timer circuit means is further provided for maintaining said lower second sound level of noise at a substantially constant level for a second period of time between 2 minutes and 7 minutes.

4. A baby calmer device in accordance with claim 1 wherein power for operating the calmer device is switched on by a manual switch and wherein the device further includes means connected to said generator means and said reducing means, for switching off said power automatically at the end of the second period of time.

5. A baby calmer device in accordance with claim 1, wherein the entire device is packaged in a housing having the shape of a sea shell.

6. A baby calmer device in accordance with claim 1 comprising:
first timing circuit means for producing a first binary output having a high output for a time duration of said initial sound level and a low output thereafter;
second timing circuit means adapted to produce a second binary output having a high output for a time duration of said initial sound level and for a time duration of said lower second sound level and a low output thereafter;
voltage generating means coupled for receiving said first and second binary outputs and further for generating a voltage output having a first level when both of said binary outputs have a high output, a second lower level when only said second binary output has a high output, and a zero output when both binary outputs have a low output;
random noise source means having a zener diode connected to said voltage output and operable for producing said noise at levels proportional to the levels of said voltage output;
amplifier means connected to said random noise source means for producing an amplified noise signal;
cut-off filer means connected to said amplifier means and adapted to filter out from said amplified noise signal the frequency components above said audio frequency range; and
converter means connected to said filter means for converting said amplified noise signal into audio noise.

7. A baby calmer in accordance with claim 6, wherein said voltage generating means further includes a transistor having a base connected to said first and second binary outputs via respective coupling resistors, a collector connected to a source of power, preferably a battery, and an emitter coupled to said zener diode of said random noise source.

8. A baby calmer device in accordance with claim 6 wherein said amplifier means further includes first and second operational amplifiers connected in series with said cut-off filter disposed therebetween.

9. A baby calmer device in accordance with claim 8, wherein said converter means for converting said amplified noise signal into audio noise further includes a transformer driven in a push-pull configuration by two push-pull amplifiers.

10. A baby calmer device in accordance with claim 9 wherein said first and second operational amplifiers and said two push-pull amplifiers are defined on a single chip.

11. A baby calmer device in accordance with claim 6 wherein each of said first and second timer circuit means is formed by a respective pair of NOR-gates coupled together via a respective R.C. timing circuit; and wherein the two pairs of NOR-gates are defined on a C-MOS chip.

12. A baby calmer device in accordance with claim 1 wherein said generator means is further operable for generating pseudo-random noise.

13. A baby calmer device in accordance with claim 1 wherein said generator means is further operable for generating random noise.

14. A baby calmer device for producing when energized a single sequence of sound levels adapted to calm a crying baby, comprising:
first timing circuit means adapted to produce a first timer output having an active output signal for a first time duration corresponding to an initial sound level time period and an inactive output thereafter;
second timing circuit means adapted to produce a second timer output having an active output signal for said duration of said initial sound level time period plus a second time duration of a second sound level time period and an inactive output thereafter;

a voltage generating means coupled to said first and second timer outputs and adapted to generate a voltage output having a first level when both said timer outputs have active output signals, a second lower level when only said second timer output has an active output signal, and a zero output when both timer outputs have inactive output signals;

noise source means having a zener diode connected to said voltage output operable for producing a noise signal the level of which being proportional to said voltage output level;

amplifier means connected to said noise source means for producing an amplified noise signal;

cut-off filter means connected to said amplifier means and adapted to filter out from said amplified noise signal the frequency components above an audio frequency range extending up to at least two thousand hertz; and converter means connected to said filter means for converting said amplified noise signal into audio noise.

* * * * *